United States Patent [19]

Englaender

[11] Patent Number: 5,231,215

[45] Date of Patent: Jul. 27, 1993

[54] METHOD OF MANUFACTURING SUBSTITUTED MONOAMIDES OF DICARBOXYLIC-ACID MONOALKYL ESTERS

[75] Inventor: Fritz Englaender, Bonn, Fed. Rep. of Germany

[73] Assignee: Huls Aktiengesellschaft, Marl, Fed. Rep. of Germany

[21] Appl. No.: 739,062

[22] Filed: Aug. 19, 1991

[30] Foreign Application Priority Data

Nov. 5, 1990 [DE] Fed. Rep. of Germany ....... 4035078

[51] Int. Cl.$^5$ .................. C07C 229/04; C07C 229/24; C07C 229/28; C07C 229/32

[52] U.S. Cl. ...................................... 560/36; 560/37; 560/155; 560/171

[58] Field of Search ................... 560/36, 37, 155, 171

[56] References Cited

FOREIGN PATENT DOCUMENTS 918155 2/1963 United Kingdom.

OTHER PUBLICATIONS

Zapeda et al. Tetrahedron, 45(2) 6439–48 (1989).
Pawlak et al. J. Org. Chem., 52(13), 2896–901 (1987).
March et al. Advanced Organic Chemistry 3rd ed. (1985).
Vorob'eva et al. Zhurnal Obshche Khimii 50(11), 2525–31, 1980.
Literature Cited, 1981, pp. 2043–2048, "Reactions of Fe(II)-Coordinated Monocarbonitriles and Monocarcoxamides".
Literature Cited, 1981, pp. 2043–2048, "Reactions of Fe(II)-Coordinated Monocarbonitriles and Monocarcoxamides".

*Primary Examiner*—José G. Dees
*Assistant Examiner*—Joseph M. Conrad
*Attorney, Agent, or Firm*—Sprung Horn Kramer & Woods

[57] ABSTRACT

A method of preparing a compound of the formula $$\begin{array}{c} COOR_1 \\ | \\ (R_4CR_3)_n \\ | \\ CONH(CH_2)_m R_2 \end{array} \qquad I$$

in which
$R_1$ is $CH_3$ or $C_2H_5$,
n is 0 to 4,
m is 1 to 3,
$R_2$ is H, $-COOR_1$, alkyl or aryl, and
$R_3$ and $R_4$ each independently is H, alkyl or aryl, which comprises reacting an alkyl ester of a dicarboxylic acid of the formula $R_1OOC-CR_3R_4-COOR_1$ with a nitrile of the formula $N\equiv C-(CH_2)_m R_2$ and with hydrogen in the presence of a hydrogenation catalyst.

4 Claims, No Drawings

METHOD OF MANUFACTURING SUBSTITUTED MONOAMIDES OF DICARBOXYLIC-ACID MONOALKYL ESTERS

The invention relates to a method of manufacturing compounds of the formula

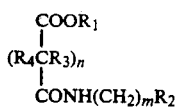

in which
$R_1$ is $CH_3$ or $C_2H_5$,
n is 0 to 4,
m is 1 to 3,
$R_2$ is H, $-COOR_1$, alkyl or aryl, and
$R_3$ and $R_4$ each independently is H, alkyl or aryl.

Substituted monoamides are generally synthesized from dicarboxylic acids by reacting a monoester acid with the corresponding amino compound in the presence of a water-binding agent, dicyclohexylcarbodiimide for example, or by reacting the amino compound with the monohalogenide of the carboxylic acid ester and binding the resulting hydrogen chloride with tertiary amines or other basic compounds that do not react with the reactants.

Both approaches have drawbacks. Monoester acids obtained from dicarboxylic acid esters are often accompanied by dicarboxylic acid. The amino compounds are in many cases obtained from nitriles, in which case the primary amines are often contaminated with secondary amines. Amines such as β-aminopropionic acid esters readily condense with themselves. The carbodiimides needed to bind the water are expensive reagents; the by-product substituted urea must be eliminated.

Chlorides of monoester acids require conversion of the acids into the carboxylic-acid chlorides, eliminating the by-product HCl and $SO_2$, and, when the acid chloride is being reacted with the amino compound, converting the hydrochlorides of the added tertiary amines into the free amine.

The known routes of preparation in accordance with Formula I are accordingly complicated and attain yields of barely 50%.

It has now been found that compounds of the Formula I can be prepared in a single stage and in high yields if the dicarboxylic acid esters are reacted with the corresponding nitriles and hydrogen under hydrating conditions in the presence of hydrogenation catalysts. There follows one example of the reaction:

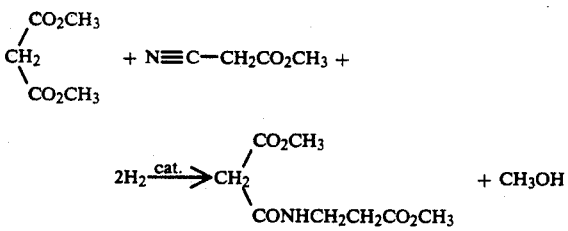

The reaction occurs at 100° to 250° C. and preferably at 170° to 210° C. The hydrogen pressure is 50 to 250 and preferably 80 to 110 bar.

The preferred catalyst is Raney nickel, although other supported-nickel catalysts can also be employed. Palladium on carbon resulted in a reaction mixture with numerous by-products. Platinum on carbon was ineffective. When Raney nickel is employed as a catalyst, it is used in no more than 5% and generally only 0.04% to 3.0% by weight of all components of the reaction, with the preferred range being 0.1% to 0.4% by weight. When a supported-nickel catalyst is employed, the amount of metal equals the amount of Raney nickel. The catalyst can be used over again, in which case adding approximately 10% fresh catalyst to each batch is recommended.

The nitrile component, $N\equiv C-(CH_2)_mR_2$, is preferably alkyl cyanoacetate, acetonitrile, benzonitrile, benzylcyanide or propionitrile.

The dicarboxylic-acid component, $R_1OOC-CR_3-R_4-COOR_1$, is preferably a dialkyl ester of malonic or oxalic acid. The alkyl in each component is preferably a radical with 1 to 6 carbon atoms and especially preferably 1 or 2 carbon atoms, and the aryl is preferably a single ring with or without additional substituents. A highly preferable $R_2$ is the group $CO_2R_1$.

The nitrile component is preferably added during the reaction and especially as it proceeds, to prevent the creation of secondary amines and to facilitate control of heat tonality. The dicarboxylic acid esters are added in excess. Preferably 2 to 10 and very preferably 3 to 5 moles of dicarboxylate are added per mole of nitrile component.

The stages following the reaction are very simple. The catalyst is filtered out and the more volatile components, usually methyl alcohol, and dicarboxylic acid ester, which is present in excess, are distilled out. The recovered dicarboxylic acid ester can, once the portion consumed in the reaction has been replaced, be employed for the next batch.

The product is purified by distillation or crystallization, depending on its physical properties. It will in many applications be pure enough for subsequent reaction without being distilled or crystallized.

The resulting acid amides can, especially when the nitrile component contains additional functional groups, esters for example, be employed as intermediate products for the synthesis of pharmaceuticals for example (German OS 1 695 644 and Journal of Antibiotics 2 [1980], 173–81).

EXAMPLE 1

Monomethyl-malonate β-alanine methyl-ester amide 1200 g of dimethyl malonate and 1.5 g of Raney nickel are added to a high-pressure autoclave, the air is forced out with nitrogen, and the nitrogen with hydrogen. The contents are simultaneously stirred and heated to 180° C. Once the temperature has attained 180° C., the pressure of the $H_2$ is adjusted to 100 bar, and 198 g of methyl cyanoacetate are added with a compression pump, a procedure that takes 2 hours. To keep up with the reaction the $H_2$ pressure is allowed to fluctuate between 100 and 85 bars. The addition of cyanoacetate is discontinued and 5 minutes later the pressure ceases to drop The hydrogen is blown off and displaced with nitrogen. The reaction mixture is removed and filtered off from the catalyst. Methyl alcohol and excess malonate are distilled off. 915 g of malonate are recovered. It has a content of 99% and can be reused. The residue is distilled in a short-route still.

b.p.$_{0.1}$:140°–145° C.

Yield: 369.3 g, 91% of theoretical $C_8H_{13}NO_5$.

|  | C | H | N | MW |
| --- | --- | --- | --- | --- |
| Calculated: | 47.3 | 6.4 | 6.9 | 203 |
| Found: | 47.0 | 6.3 | 7.1 | 203 |

EXAMPLE 2

The procedure follows Example 1 except that the catalyst is 6 g of RCH 55/5 TS (Hoechst AG), a 55% by weight supported nickel catalyst. The reaction and follow-up in no way differ from Example 1.

Yield: 85% of theoretical.

EXAMPLE 3

As in Example 1, except that the catalyst is allowed to settle for 15 minutes subsequent to hydration. The reaction mixture is then removed with a submerged coil and 1200 g of methyl malonate and 0.2 g of Raney nickel added, whereupon hydration proceeds at 190° C. as described in Example 1. The procedure is then repeated with another 0.2 g of Raney nickel added to the malonate.

| Batch No. | Yield % theoretical |
| --- | --- |
| 1. | 88.5 |
| 2. | 87.9 |
| 3. | 85 |

EXAMPLE 4

Monoethyl-malonate β-alanine ethyl-ester amide 1080 g of diethyl malonate and 3 g of Raney nickel are added to a high-pressure autoclave, the air is forced out with nitrogen, and the nitrogen with hydrogen. The contents are simultaneously stirred and heated to 180° C. Once the temperature has attained 180° C., the pressure of the $H_2$ is adjusted to 100 bar, and 169.5 g of ethyl cyanoacetate are added with a compression pump, a procedure that takes 2 hours. To control the uptake of hydrogen, its pressure is allowed to fluctuate between 100 and 90 bar. The addition of cyanoacetate is discontinued and the absorption of $H_2$ terminates a few minutes later. The hydrogen is blown off and displaced with nitrogen. The reaction mixture is removed, the catalyst filtered off, and the reaction product fractionated.

b.p.$_{0.1}$: 140°–150° C.

Yield: 306.5 g, 88.5% of theoretical $C_{10}H_{17}NO_5$.

|  | C | H | N | MW |
| --- | --- | --- | --- | --- |
| Calculated: | 51.9 | 7.4 | 6.1 | 231 |
| Found: | 51.5 | 7.4 | 6.0 | 231 |

EXAMPLE 5

Monoethyl-oxalate β-alanine ethyl-ester amide 1200 g of diethyl oxalate, 3 g of Raney nickel, and 226 g of ethyl cyanoacetate are reacted as described with reference to Example 4.

b.p.$_{0.1}$: 118°–121° C.

Yield: 312.5 g, 72.0% of theoretical $C_9H_{15}NO_5$.

|  | C | H | N | MW |
| --- | --- | --- | --- | --- |
| Calculated: | 49.8 | 6.9 | 6.5 | 217 |
| Found: | 50.1 | 6.8 | 6.7 | 217 |

EXAMPLE 6

Monomethyl malonate, N-ethyl amide 1200 g of dimethyl malonate, 3 g of Raney nickel, and 82 g of acetonitrile are converted as described with reference to Example 4 b.p.$_{0.1}$: 92°–93° C.

Yield: 230.5g, 79.5% of theoretical $C_6H_{11}NO_3$.

|  | MW |
| --- | --- |
| Calculated: | 145 |
| Found: | 145 |

EXAMPLE 7

Malonic acid, 3-oxo-3-(2-phenylethylamino)-, methyl ester 1200 g of dimethyl malonate, 3 g of Raney nickel, and 234 g of benzyl cyanide are reacted as described in Example 4.

m.p.: 70° C.

Yield: 369 g, 83.5% of theoretical $C_{12}H_{15}NO_3$.

|  | C | H | N | WM |
| --- | --- | --- | --- | --- |
| Calculated: | 65.2 | 6.8 | 6.3 | 221 |
| Found: | 65.0 | 6.8 | 6.5 | 221 |

EXAMPLE 8

Malonic acid, 3-oxo-3-(benzylamino)-, methyl ester 1200 g of dimethyl malonate, 3 g of Raney nickel, and 208.3 g of benzonitrile are reacted as described in Example 4.

m.p.: 67° C.

Yield: 385.3 g, 92% of theoretical $C_{11}H_{13}NO_3$.

|  | C | H | N | MW |
| --- | --- | --- | --- | --- |
| Calculated: | 63.8 | 6.3 | 6.8 | 207 |
| Found: | 64.1 | 6.3 | 6.6 | 207 |

It will be understood that the specification and examples are illustrative but not limitative of the present invention and that other embodiments within the spirit and scope of the invention will suggest themselves to those skilled in the art.

What is claimed is:

1. A method of preparing a compound of the formula

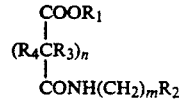

I in which $R_1$ is $CH_3$ or $C_2H_5$, n is 0 to 4, m is 1 to 3, $R_2$ is H, $-COOR_1$, alkyl or aryl, and $R_3$ and $R_4$ each independently is H, alkyl or aryl, which comprises reacting an alkyl ester of a dicarboxylic acid of the formula $R_1OOC-CR_3R_4-COOR_1$ with a nitrile of the formula $N\equiv C-(CH_2)_mR_2$ and with hydrogen in the presence of a hydrogenation catalyst.

2. A method according to claim 1, wherein the nitrile is added during the reaction.

3. A method according to claim 1, wherein the reaction temperature is about 100° to 250° C.

4. A method according to claim 1, wherein the hydrogenation catalyst is or contains nickel.